United States Patent [19]

Brothers

[11] Patent Number: 5,380,355
[45] Date of Patent: Jan. 10, 1995

[54] AIRSTREAM DECONTAMINATION UNIT

[75] Inventor: Larry P. Brothers, Manchester, Tenn.

[73] Assignee: Lebone Corporation, Tullahoma, Tenn.

[21] Appl. No.: 57,543

[22] Filed: May 6, 1993

[51] Int. Cl.⁶ ............................................. B03C 3/10
[52] U.S. Cl. .................................. 96/64; 55/360; 95/77; 95/78; 96/94; 96/97
[58] Field of Search .............. 96/94, 62, 97, 64; 95/77, 78; 55/360

[56] References Cited

U.S. PATENT DOCUMENTS

| | | | |
|---|---|---|---|
| 640,694 | 1/1900 | Otto | 96/94 X |
| 3,509,695 | 5/1970 | Egan et al. | 55/360 X |
| 3,519,551 | 7/1970 | Pechuro et al. | 204/171 X |
| 3,785,117 | 1/1974 | Leith | 95/77 X |
| 3,839,185 | 10/1974 | Vicard | 55/360 X |
| 4,268,385 | 5/1981 | Yoshikawa | 210/150 |
| 4,386,055 | 5/1983 | McBride | 422/186.18 |
| 4,832,918 | 5/1989 | Horikoshi et al. | 422/186.18 |
| 5,084,077 | 1/1992 | Junker et al. | 96/39 |

FOREIGN PATENT DOCUMENTS

| | | | |
|---|---|---|---|
| 713691 | 10/1931 | France | 95/77 |
| 171709 | 12/1934 | Switzerland | 96/94 |

Primary Examiner—Richard L. Chiesa
Attorney, Agent, or Firm—Edward D. Lanquist, Jr.; Mark J. Patterson

[57] ABSTRACT

A waste airstream decontamination unit has a series of grounded electrodes extending vertically from rotating shafts mounted transversely across a decontamination chamber. Corresponding upper and lower positive electrodes extend toward the rotating grounded electrodes in an angular relationship. Rotation of the shafts causes the charged electrodes to produce and sustain a repeating sequence of arcs which ionize and control the airborne contaminants which are passed through the chamber.

4 Claims, 7 Drawing Sheets 5,380,355

AIRSTREAM DECONTAMINATION UNIT

BACKGROUND OF THE INVENTION

The present invention relates generally to the control of airborne chemical contaminants and more particularly to an apparatus for removal of chemical contaminants from a waste airstream.

It will be appreciated by those skilled in the art that the control of waste byproducts of combustion and other industrial processes which produce waste airstreams has become increasingly important and difficult. For example, many municipalities and solid waste processing companies use incineration as a means for reducing the amount of solid waste. However, the process of incineration itself often produces excessive and undesirable airborne toxins and other chemical contaminants which, if not controlled and removed, would be released through a waste air stack to the atmosphere. Accordingly, a number of techniques and devices have been tried over the years in order to control these waste airstream contaminants, including inertial separation, chemical scrubbing, mechanical filtration, electrostatic precipitation, electron beam irradiation, and chemical catalytic devices. Each of these methods has achieved some success in certain applications but significant problems remain.

For example, most prior art airborne waste control systems work well on relatively large-sized particulates suspended in the airstream but are not as effective in removal of relatively fine or small particles mixed in the gas. Catalytic beds and chemical scrubbing systems are highly sensitive to precise temperature control and the gas and airborne particulates can poison the catalyst thereby reducing its effectiveness.

Electrostatic precipitation systems have been widely used to control airborne contaminants in waste airstreams. Such systems use arrays of electrodes to which is applied a high voltage so that any gas near the electrodes is ionized. Particles suspended in the gas then are charged from contact with the gas ions whereby such charged particles then migrate to an oppositely charged electrode. The accumulated particulates are then mechanically removed from the ionization chamber. These systems, however, are limited in that only solid particulate matter can be removed, they do not work on all particulate materials, and there is a significant trade off in ionization efficiency as a function of flow rate of the waste airstream through the precipitation unit.

What is needed, then, and not found in the prior art, is a waste airstream decontamination unit which is effective in removing harmful airborne contaminates regardless of their size or chemical composition and which is effective at doing so at relatively high airstream flow rates. This device is presently lacking in the prior art.

SUMMARY OF THE INVENTION

In the present invention, a waste airstream is drawn through an intake pipe into a decontamination chamber by a blower connected to a gas discharge line. The interior of the chamber is separated by baffles into two sections. In each section is contained at least one set of positive and grounded electrode pairs. Positive electrodes are mounted in an angular relationship to plates suspended across tile chamber above and below a sequence of rotating shafts. Grounded electrodes extend vertically from the rotating shafts such that each grounded electrode is arranged in an angular arc sustaining relationship proximate to a positive electrode.

A drive motor is coupled to each rotating shaft on the exterior of the decontamination chamber such that rotation of the drive motor pulley causes synchronous rotation of the electrode shafts within the chamber. A ten-thousand volt AC potential is then applied across the positive and grounded electrodes. As the grounded electrodes are rotated and are moved in close proximity to a corresponding positively charged electrode, an arc is formed which then travels along the electrodes in conjunction with movement of the grounded electrodes. The baffles which separate the chamber sections have openings which cause the airstream to impinge on the area where the arcs are being produced. The waste airstream, then, which is being forced and directed through the decontamination chamber, is subjected to the resulting ionization and decontamination effects of the arcs.

DESCRIPTION OF THE PREFERRED EMBODIMENT

Figure 1:
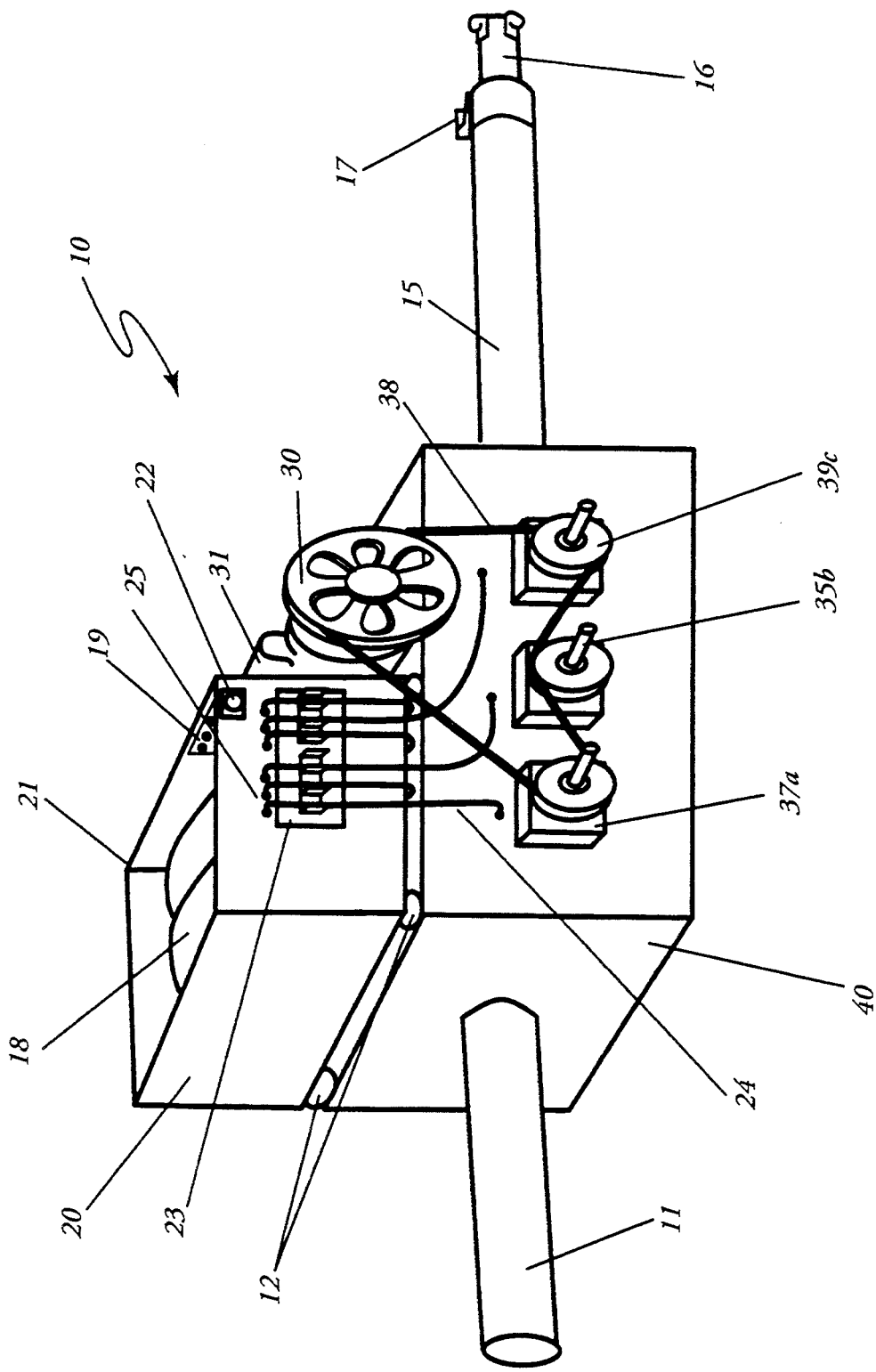
FIG. 1 is a perspective view of the waste airstream decontamination unit of the present invention.
Figure 2:
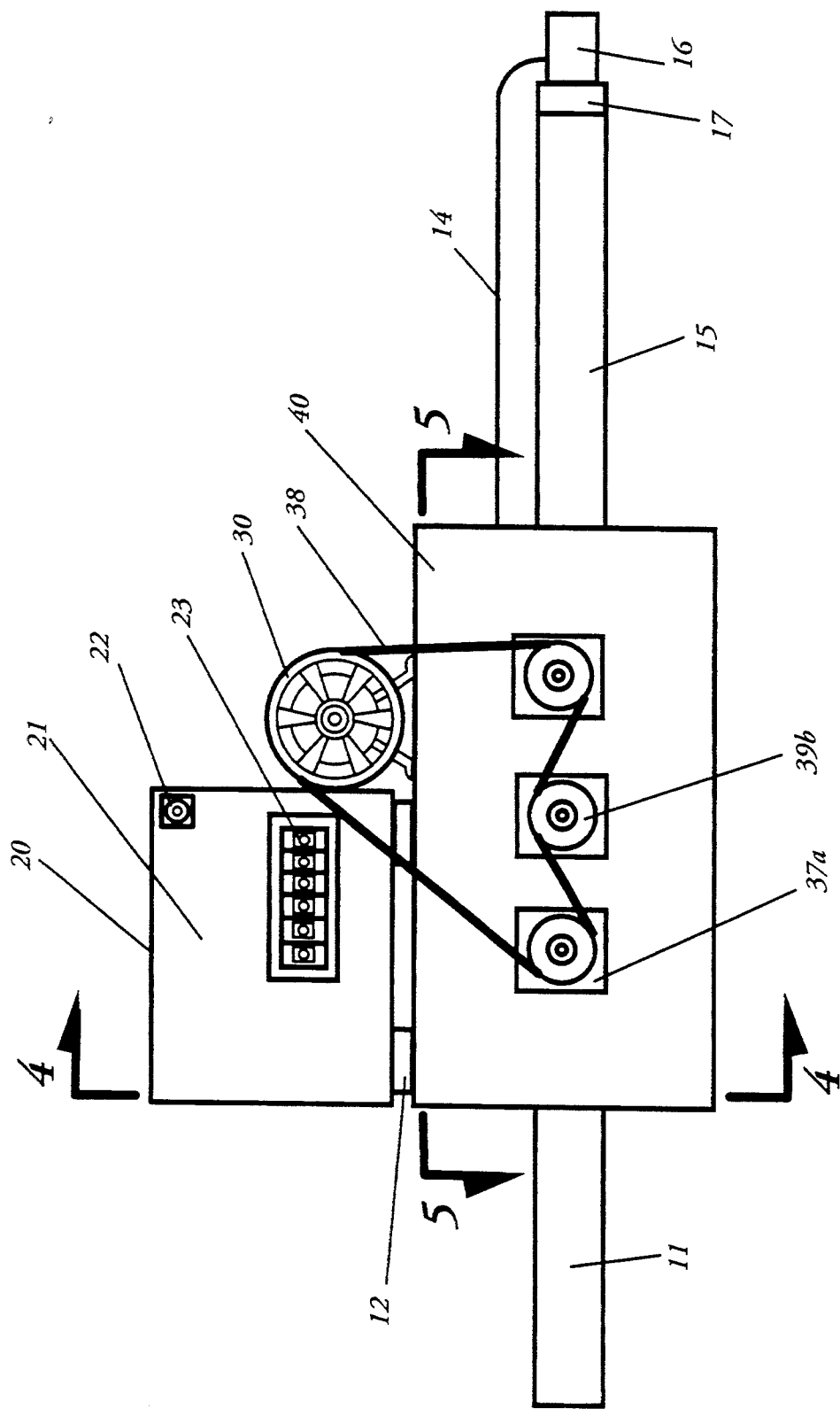
FIG. 2 is a side view of the waste airstream decontamination unit of the present invention.
Figure 3:
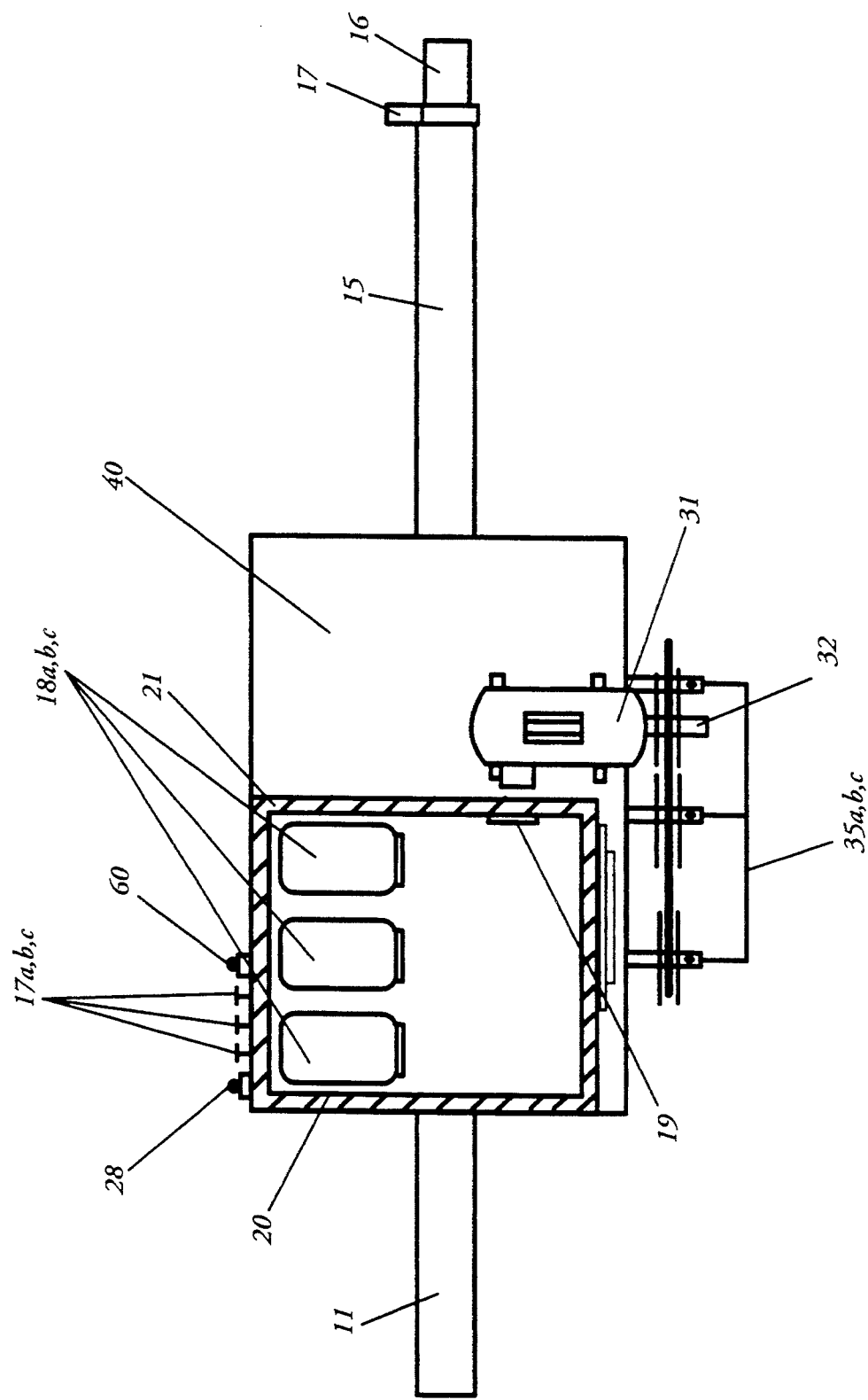
FIG. 3 is a top view of the waste airstream decontamination unit of the present invention with the top of the control box removed.

Referring to FIGS. 1, 2, and 3, the waste airstream decontamination unit 10 of the present invention is seen. Air intake 11 is bolted or welded to the enclosure 41 of a decontamination chamber 40 such that a waste airstream and its contaminants are introduced into chamber 40 in a relationship that is sealed from the ambient environment. Enclosure 41 can be made of 5/16" mild steel plate. The waste airstream is drawn into chamber 40 by a blower assembly 17 which is driven by blower motor 16. Blower 17 and blower motor 16 are attached in line with gas discharge line 15 which, in turn, is bolted or welded to enclosure 41 on the discharge side of decontamination chamber 40. The size and capacity of blower 17, blower motor 16, chamber 40, and intake and discharge lines 11 and 15 will vary depending on the application. In one preferred embodiment usable for relatively low volume waste airstreams, 0.16 L(liters) PM to 0.32 LPM for example, blower 17 is a standard 3" squirrel cage blower. Enclosure 41 is approximately 32" long, 17" high, and 17" deep. Intake and discharge lines 11 and 17 are 3" diameter 40 gauge steel pipes.

A control box 20, which includes housing 21, is mounted to the top surface of enclosure 41 of decontamination unit 40. Control box housing 21, made of ⅛" aluminum plating or other suitable material, is electrically isolated from decontamination chamber enclosure 41 by non-conductive insulating pads 12, preferably at least 1" thick. Adjacent to control box 20 and mounted also to the top surface of decontamination chamber enclosure 41 is drive motor 31. A primary drive pulley 30 is mounted to drive motor shaft 32. A series of three laterally aligned electrode drive shafts 35a, 35b, and 35c extend through and outward from the side panels of decontamination chamber enclosure 41. Corresponding secondary drive pulleys 39a, 39b, and 39c are mounted to each electrode drive shaft 35. A drive belt 38 operatively connects primary drive pulley 30 to secondary drive pulleys 39a, 39b, and 39c such that outside drive pulleys 39a, and 39c are turned clockwise while inside drive pulley 39b is turned counterclockwise. Again, the size and capacity of motor 31 and primary drive pulley 30, and secondary drive pulleys 39 will depend on the decontamination capacity demanded by the specific application. In the preferred embodiment described herein, drive motor 31 is a 1 HP 110 VAC electric motor operated at approximately 1125 RPM. Primary drive pulley 30 has an 8" diameter. Secondary drive pulleys are 4" in diameter such that each shaft 35 is rotated at approximately 2250 RPM.

A series of three upper electrode power feed wires 24 and lower electrode power feed wires 25 pass from within and through the side panel of control box housing 21 where they are mechanically stabilized at wiring connection panel 23. A power feed line plug 22 also extends through the side wall of control unit housing 21 to allow the connection of external AC power to unit 10. Blower motor 16 receives power through cable 14.

Looking specifically now at FIG. 3, further detail of control box 20 is shown. AC power transformers 18a, 18b, and 18c are mounted to the lower interior surface of control box housing 21. Transformers 18 are of conventional design with a primary input voltage of 110 v with a secondary voltage of 10,000 VAC. Mounted to the exterior of the opposite or back side wall of control box housing 21 is a primary power switch 28 as well as three transformer power switches 17a, 17b, and 17c and a drive motor control switch 60. Appropriate interconnections between transformers 18, switches 17, 28, and 60, AC power feeder plug 22, upper and lower power feed wires 24, 25, and other electrical components as will be discussed below, are made in a conventional manner interior to control box 20 at wiring panel 19.

Figure 4:
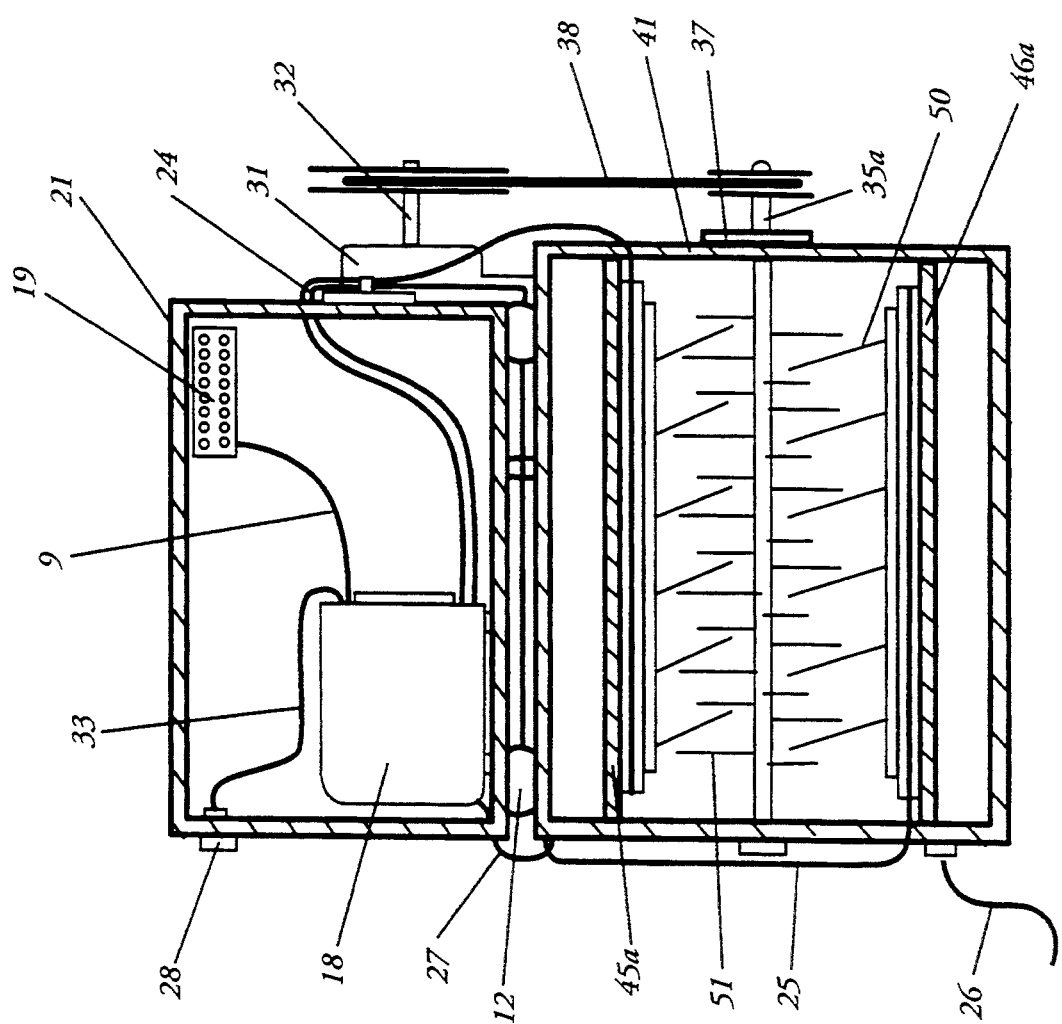
FIG. 4 is a sectional end view of the interior of the waste airstream decontamination unit, taken along line A—A as shown on FIG. 2.
Figure 5:
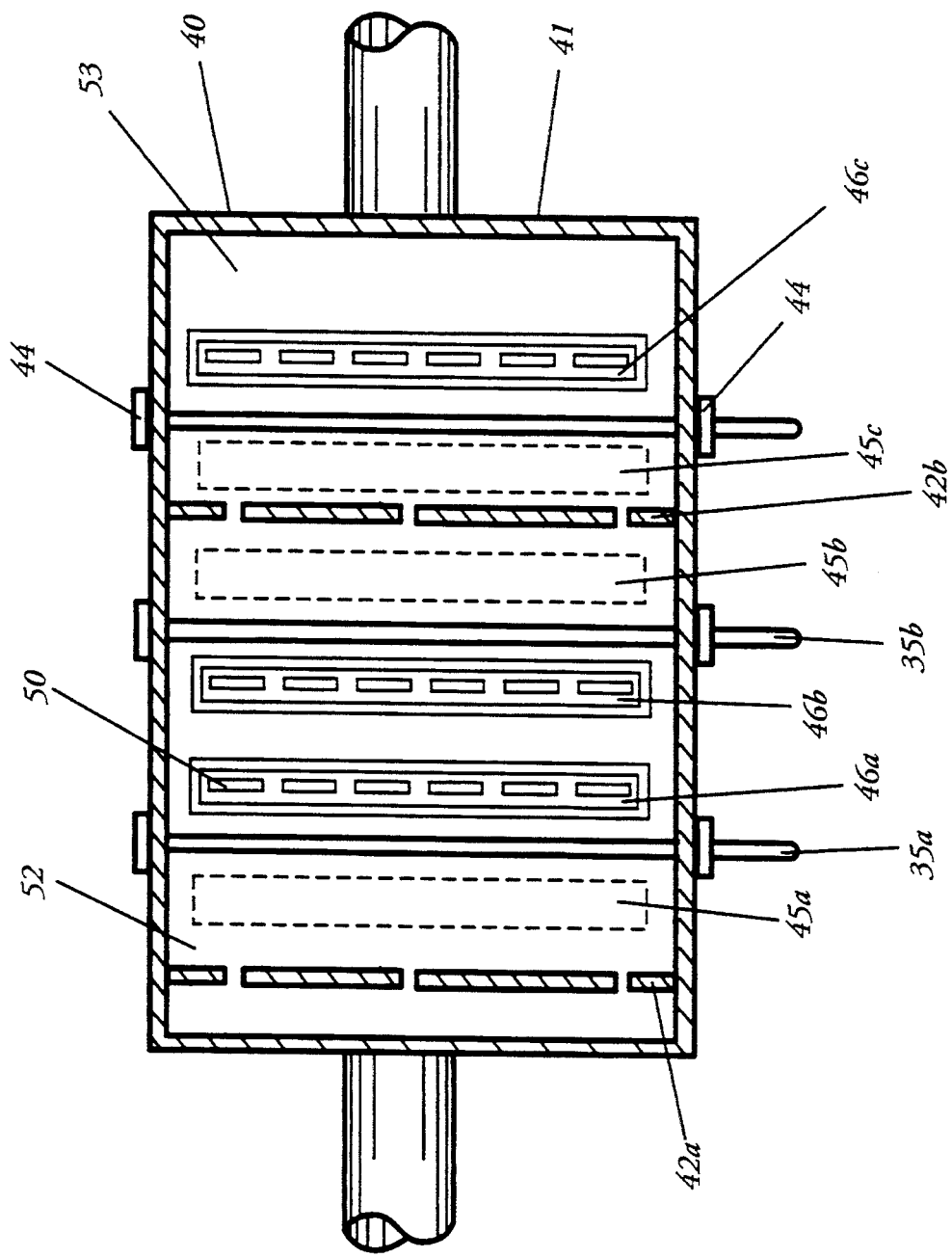
FIG. 5 is a top sectional view of the interior of the decontamination chamber of the present invention, taken along line B—B of FIG. 2.

Looking now at FIGS. 4 and 5, the interior of decontamination chamber 40 of the present invention can be seen. Extending transversely across decontamination chamber 40 are baffle plates 42a and b which divide the interior of chamber 40 into first section 52 and second section 53. Electrode shafts 35a, 35b, and 35c also extend transversely across chamber 40 and are supported by bearings 44 at the side walls of enclosure 41. Shafts 35a and 35b are positioned within first section 52 of chamber 40. Electrode drive shaft 35c is positioned within second section 53 of chamber 40.

Three upper mounting plates 45a, 45b, and 45c extend across chamber 40 and are attached near the upper margin of side walls of enclosure 41. Three lower mounting plates 46a, 46b, and 46c extend across and are attached near the lower margin of the side walls of enclosure 41 of chamber 40. Upper and lower mounting plates 45a, 45b, and 45c and 46a, 46b, and 46c are positioned such that they are longitudinally aligned with electrode drive shafts 35a, 35b, and 35c but, as best seen in FIG. 5, are offset both from each other and from their corresponding electrode drive shaft 35.

Extending vertically from each electrode drive shaft 35 are a plurality of grounded electrodes 51. In the preferred embodiment, for each electrode drive shaft 35 there are four aligned sets of electrodes 51, each set containing six linearly aligned electrodes, and each set positioned ninety degrees apart circumferentially around electrode drive shaft 35.

Figure 7:
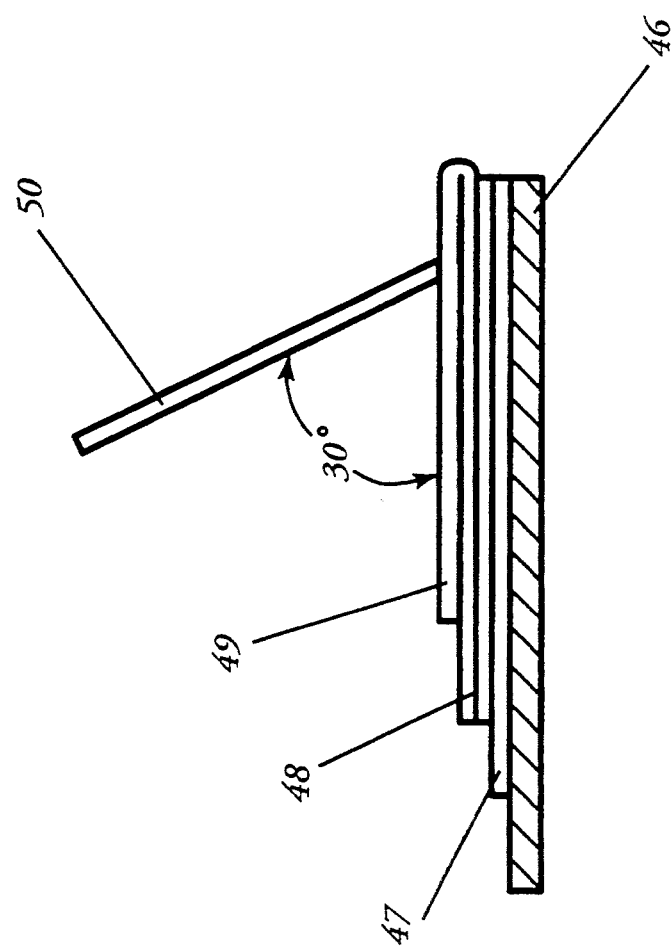
FIG. 7 is an enlarged view of a positive electrode and its mounting components as used in the decontamination chamber of the present invention.

Looking now at FIGS. 4 and 7, further detail about upper and lower mounting plates 45 and 46 can be seen. Attached to the downward facing surface of upper mounting plates 45 and to the upward facing surface of lower mounting plates 46 are insulating plates 47, made of ⅜" thick fiberglass or other suitable electrical insulating material. Attached to insulating plates 47 are power connection bars 48, preferably made of ¾" copper bar, and electrode mounting bars 49, preferably made of ⅜" copper. Extending at an angular relationship with respect to electrode mounting bars 49 are plural linearly aligned angled positive electrodes 50.

In a preferred embodiment, electrodes 50 and 51 are made of a metal having the ability to withstand the high temperatures associated with electric arcs, such as tungsten.

Power connector bars 48 associated with upper mounting plates 45a, 45b, and 45c are electrically connected to corresponding transformers 18a, 18b, and 18c by upper power feed wires 24. The power connector bars 48 associated with lower mounting plates 46a, 46b, and 46c are electrically connected to corresponding transformers 18a, 18b, and 18c by lower power feed wires 25. Enclosure 41 of decontamination chamber 40 is electrically grounded by first ground wire 26. Each transformer 18a, 18b, and 18c is also grounded by means of second ground wire 27 which is electrically connected to enclosure 41 of chamber 40. Electrode drive shafts 35, preferably made of 1" diameter steel rod, are also grounded by means of their electrical contact with chamber enclosure 41 through bearings 44. However, insulating plates 37a, b and c electrically isolate the exterior section of each shaft 35 as well as attached secondary drive pulleys 39.

Figure 6:
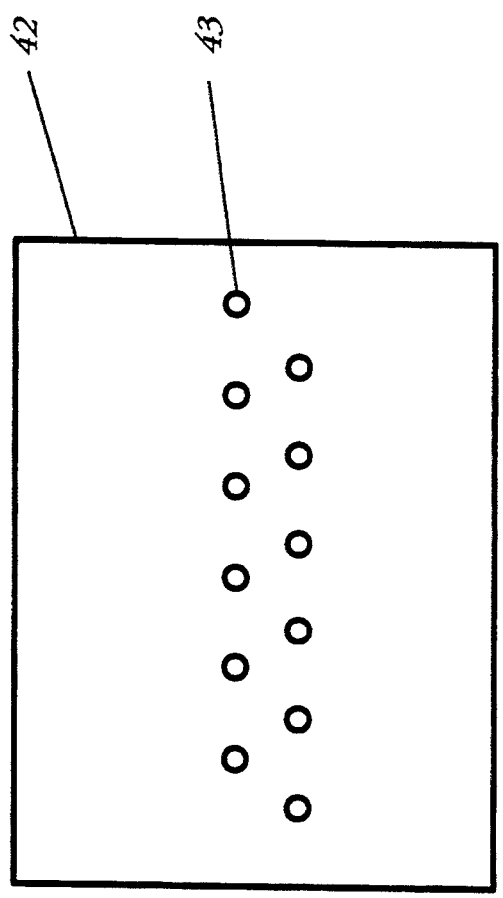
FIG. 6 is a side view of a baffle plate as found in the decontamination chamber of the present invention.

The geometry of baffle plates 42 is shown in greater detail on FIG. 6. Each baffle plate 42a and 42b is attached by welding or otherwise to the top, bottom and side walls of enclosure 41. Two sets of linearly aligned openings 43 extend through each baffle plate 42 to provide a passage for the waste airstream between first decontamination unit section 52 and second section 53. The upper set of openings 43 are positioned so as to correspond to the point of closest convergence between positive electrodes 50 and grounded electrodes 51 such that waste gases are directed proximate to the area of arcing.

It is important in an airstream decontamination unit of the type described as in the present invention that the contact between the waste airstream and the electrical arcs being produced within decontamination chamber 40 be maximized. Accordingly, the geometry and configuration of the electrodes and related components have been designed to maximize that effect, recognizing that proportional changes may be made if increased decontamination capacity is needed. In the preferred embodiment, each electrode shaft 35 has a total of twenty-four (24) electrodes 51, or four (4) linearly aligned rows of six (6) electrodes 51, each row or set being spaced ninety degrees (90°) around shaft 35.

Within each row, each electrode 51 is spaced approximately two inches (2") apart with a nominal length of approximately four and one-quarter inches (4¼"). Also each shaft 35 is positioned so that its center line is approximately five inches (5") from the lower facing surface of electrode mounting bars 49, with a preferred tolerance of ±1/64".

The positive electrodes 50 extend away from mounting bars 49 at a thirty degree (30°) angle with a preferred tolerance of +1, −2 degrees. Electrodes 50 are also approximately four and one-quarter inches (4¼") in length, and spaced approximately 2" apart, such that during rotation of shafts 35, grounded electrodes 51 pass no closer than one-eighth inch (⅛") (preferably ±1/64") to positive electrodes 51.

Using this configuration and geometry, optimum arc position and duration is achieved. As each grounded electrode 51 rotates with shaft 35, it approaches within one-eighth inch (⅛") of one of two corresponding positive electrodes 50 which extend from either a upper mounting plate 45 or a lower mounting plate 46. At the moment of closest convergence, an electric arc is induced at the distal ends or tips of electrodes 50 and 51. As shaft 35 continues to rotate, the arc travels diagonally down electrode 50, extending from an initial arc length of approximately one-eighth inch (⅛") to a length of approximately two inches (2") to two and one-quarter inches (2¼") diagonally. Greater decontamination effect is achieved when the arcs are longest.

In the preferred embodiment, each arc lasts approximately 0.004 seconds. At any given moment in time, there exist twelve (12) arcs per shaft, each such arc corresponding to the convergence of positive electrodes 50 above and below shaft 35 with their corresponding grounded electrode 51. As each set of grounded electrodes 51 moves away from a corresponding set of positive electrodes 50 extending from either upper mounting plate 45 or lower mounting plate 46, the next set of grounded electrodes 51 move into position. This cycle repeats approximately every 0.0394 seconds.

Although in the preferred embodiment described herein electrodes 50 and 51 have been assigned polarities for purposes of description, such polarities can be reversed without departing from the scope of the present invention. Also, the number and position of shafts 35, the number of chamber sections, and the number of electrodes 50 and 51 can be modified where more or less efficiency or capacity may be desired.

Thus, although there have been described particular embodiments of the present invention of a new and useful airstream decontamination unit, it is not intended that such references be construed as limitations upon the scope of this invention except as set forth in the following claims. Further, although there have been described certain dimensions used in the preferred embodiment, it is not intended that such dimensions be construed as limitations upon the scope of this invention except as set forth in the following claims.

What I claim is:

1. A waste airstream decontamination unit comprising:

a. a decontamination chamber;
   b. at least one rotating shaft extending across said chamber;
   c. at least one set of grounded electrodes attached to and extending away from said shaft, each of said grounded electrodes comprising a rod having a side surface and terminating at a tip,
   d. electrode mounting means extending across said chamber proximate to and in substantial alignment with each said shaft;
   e. a plurality of positive electrodes mounted to said electrode mounting means, each of said positive electrodes comprising a rod having a side surface and terminating at a tip, each of said positive electrodes arranged to correspond to at least one of said grounded electrodes, whereby rotation of said shaft will periodically place each of said grounded electrodes in an arc-producing position with respect to at least one of said positive electrodes;
   f. means for applying an arc-producing and sustaining electric potential between said positive and grounded electrodes;
   g. means for rotating said shaft;
   h. means for causing said waste airstream to flow through said chamber proximate to said positive and grounded electrodes; and
   i. each of said positive electrodes being in an angular relationship with respect to a corresponding said grounded electrode whereby when a said grounded electrode is rotated proximate to a said positive electrode, an arc is created between said tips of said positive electrode and said grounded electrode and whereby continuing rotation of said shaft will cause said arc to travel along said side surface of at least one of said electrodes as said arc extends in length.

2. The decontamination unit of claim 1 further comprising:

a. at least one baffle dividing said chamber into at least two decontamination sections, each of said sections containing at least one of said shafts and at least one of said electrode mounting means;
   b. said baffles including openings for directing the flow of said waste airstream between said sections proximate to a point of arcing between said positive and grounded electrodes.

3. The decontamination unit of claim 1 further comprising at least two sets of said grounded electrodes spaced circumferentially around said shaft, and each of said positive electrodes having an angular arc-sustaining relationship with respect to at least one of said grounded electrodes from each of said electrode sets during a single rotation of said shaft.

4. The decontamination unit of claim 1 further comprising an upper electrode mounting means above said shaft and a lower electrode mounting means below said shaft, whereby a complete rotation of said shaft will cause the creation of an arc between each of said grounded electrodes and at least one positive electrode extending from both said upper electrode mounting means and said lower electrode mounting means.

* * * * *